United States Patent
Damasco et al.

[19]

[11] Patent Number: 6,080,148
[45] Date of Patent: Jun. 27, 2000

[54] VARIABLE PULSE WIDTH LASING DEVICE

[75] Inventors: Sanford Damasco, Long Beach; Marvin P. Loeb, Huntington Beach; Randall J. Blair, Oceanside, all of Calif.

[73] Assignee: Trimedyne, Inc., Irvine, Calif.

[21] Appl. No.: 08/751,552

[22] Filed: Nov. 18, 1996

[51] Int. Cl.[7] .................................................. A61N 5/06
[52] U.S. Cl. .................................. 606/10; 606/2; 606/3; 606/11
[58] Field of Search ....................... 606/2, 3–18

[56] References Cited

U.S. PATENT DOCUMENTS 5,166,513  11/1992  Keenan et al. .
5,269,778  12/1993  Rink et al. .
5,387,211   2/1995  Saadatmanesh et al. .

OTHER PUBLICATIONS

"Selective Photothermolysis: Precise Microsurgery by Selective Absorption of Pulsed Radiation" by Anderson et al; Science. vol. 230: Apr. 24, 1983; pp. 524–527.

Xintec, Xintec Web Site ∂ www.xintec.com/tech.htm regarding Odyssey Ho:YAG. Oct. 8, 1996.
inrad, Model 2–018 Shutter driver specification.
inrad, Model 204–080D Damped Lithum Niobate Q–Switch specification.
FastPulse Technology, Inc., Lasermetrics Division, User's Guide For Lasermetric Model 8025 High Voltage Pulse Generator.
FastPulse Technology, Inc., Lasermetrics Division, User's Guide For KD*P & Lithium Niobate Q–Switches & Modulators for Q–Switching, Chopping & Pulse Extraction.

*Primary Examiner*—David M. Shay
*Attorney, Agent, or Firm*—Olson & Hierl, Ltd.

[57] ABSTRACT

A variable pulse width lasing device for selectively reducing the amount of laser energy provided during a surgical procedure is described. The device includes a central processing unit, a laser resonator, pulse width detector and a pulse modulator. The central processing unit provides a switch activation command to the modulator. The modulator also receives a laser pulse produced by the laser resonator which has an initial pulse width and a wavelength which is compatible for transmission through an optical fiber. The modulator varies the width of the laser pulse for providing an output pulse at a selected pulse width and energy level.

41 Claims, 3 Drawing Sheets

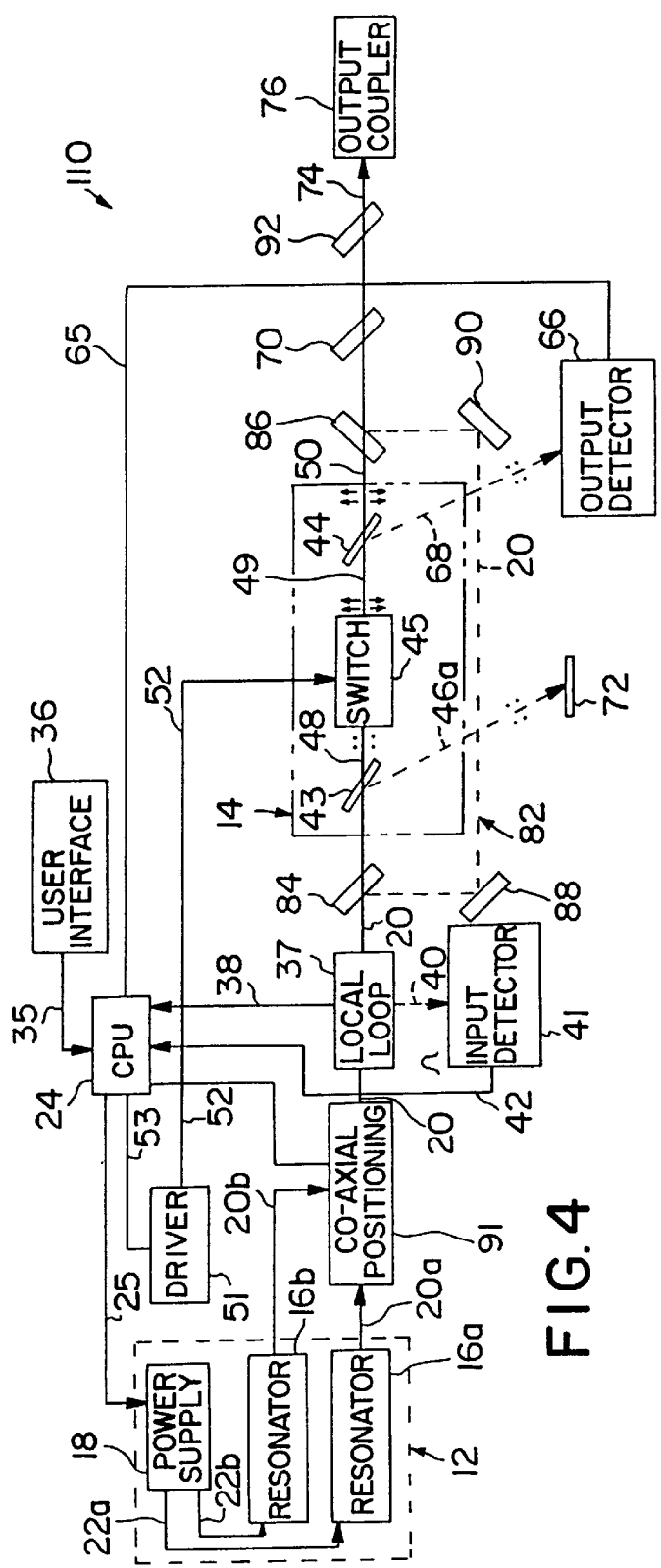
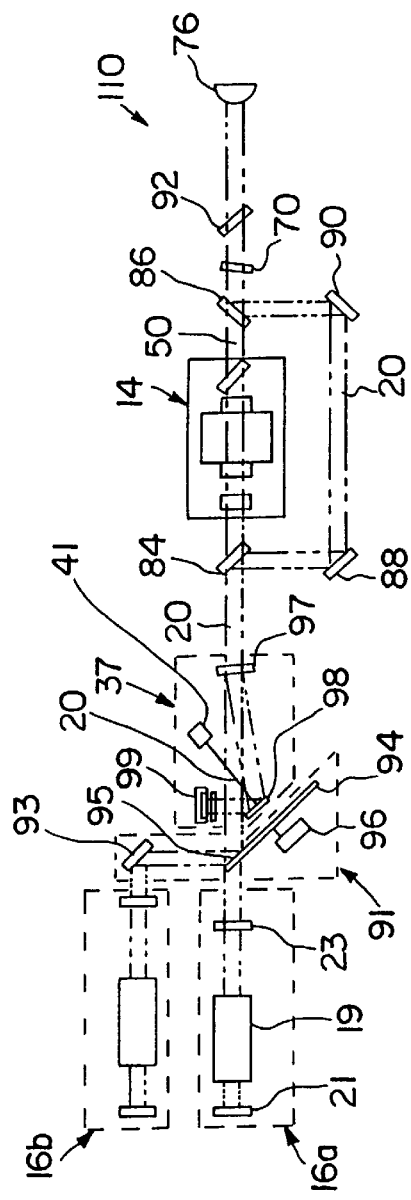
FIG. 4
FIG. 5

VARIABLE PULSE WIDTH LASING DEVICE

FIELD OF THE INVENTION

The present invention relates to surgical devices and procedures for providing laser energy, and in particular to a device and procedure for varying the energy provided by a pulsed surgical laser.

BACKGROUND OF THE INVENTION

Systems for delivering laser energy onto tissue are well known in the art. The use of laser energy provides a less invasive style of surgical intervention. This style is characterized by achieving a maximal therapeutic effect with minimal damage to surrounding and overlying normal tissues.

For performing precision surgical procedures, the laser energy can be transmitted through an optical fiber introduced via endoscopic devices which pass through the body's natural orifices, or through optical fibers inserted transdermally in minimally invasive procedures.

Wavelengths that can be effectively transmitted through an optical fiber are dependent on the propagation loss and the dispersion loss of the light as it propagates through the fiber. Therefore, the spectral bandwidth of the laser energy plays an important role in the dispersion-limited propagation, while the laser input power plays a crucial role in the absorption-limited regime.

Merely increasing the level of input power through an optical fiber, even below obvious limits of material damage, will not necessarily result in a higher output power. Nonlinear interactions such as scattering and the affects of heat due to over pumping become important at high laser intensities. Thus, transmission at both a wavelength and power level compatible with the optical fiber is the most effective way of preventing optical loss and delivering laser energy. Currently, optical energy having a wavelength in the range of less than about 3 $\mu$m can effectively travel through conventional optical fibers.

The effect of laser energy on tissue is a function of laser wavelength, energy density, time of exposure, and tissue absorption. Changing these parameters will result in a variation in the amount of heat generated in the tissue. The interaction between temperature and the affected tissue area determines whether the tissue will be cut, vaporized or coagulated by the laser energy.

As known by those skilled in the art, biological tissue comprises cells embedded in a primarily proteinaceous extracellular matrix. Collagen is one of the predominate proteins found in the extracellular matrix. Collagen can be altered by the application of energy, such as provided by a laser. At relatively low energy, collagen can be cross linked, reducing its volume and increasing shrinkage or tightening of tissue. At higher energies, collagen can be denatured and form a biological glue. For such a subcutaneous surgical procedure, it is desirable to provide pulsed laser energy at a frequency of about 20 to 80 Hertz (Hz) with each pulse providing energy in the range of about 0.1 to 30 milliJoules (mJ) or less, and preferably about 1 to 10 mJ.

As indicated previously, manipulation of the amount of laser power is a practical expedient during a surgical procedure when laser energy is transmitted through an optic fiber. The wavelength range which can be transmitted through a standard optic fiber is substantially limited however.

Two laser sources which are particularly useful in providing laser energy at a wavelength that is transmittable through an optical fiber are excimer lasers and near infra red lasers. The term excimer describes a family of lasers which emit powerful pulses lasting nanoseconds or tens of nanoseconds at wavelengths in or near the ultraviolet. Near infrared lasers are typically solid state lasers in which the active medium is a nonconductive solid, a crystalline material, or glass doped with a species that can emit laser light.

Excimer lasers and many types of solid state lasers can operate only in a pulsed mode for a variety of reasons due to internal physics. One of the most widely used medical solid state lasers, holmium, can operate in the quasi-continuous wave at cryogenic temperatures, but operates in the pulsed mode at room temperatures.

Typically, it is desirable to change the "natural" duration of the laser pulses widths in order to control the pulse energy density delivery. Mostly, the goal is to shorten each energy pulse to provide higher instantaneous peak power. Normally, the pulse repetition rate, pulse rate duration, and peak power can be adjusted by a variety of methods such as intercavity Q-switching which functions by eliminating the gain feedback inside a laser resonator, in essence storing energy in the population inversion, to produce a pulse that is shorter in width and higher in peak power than an unaltered laser emission. Correspondingly, changing the pulse width gives the laser user added flexibility in matching laser characteristics to satisfy certain operational requirements (i.e., clinical application, tissue integration, etc.).

Although Q-switching performs well with many laser types, intercavity Q-switching of excimer lasers is impractical because of the high internal gain of such lasers. Likewise, intercavity Q-switching of holmium lasers is ineffective because of the incomplete energy transfer which can result in a large pulse-to-pulse variation in pulse amplitude. Additionally, the high peak intercavity fluences can cause coating damage to the rod and the optics surface adding to the ineffectiveness and impracticality. Thus, the current methods fail to provide for precisely controlling the duration of time and, hence the amount of laser energy being emitted onto tissue.

The present invention provides a device which overcomes the above problems by selectively attenuating a laser pulse after the pulse has been emitted from a laser resonator to control the amount of energy density delivered onto tissue.

SUMMARY OF THE INVENTION

The present invention provides a surgical lasing device for effectively controlling the amount and duration of laser energy that is delivered through an optical fiber and onto the tissue of a patient.

The device embodying the present invention is especially suitable for surgical procedures in which a minimally invasive approach is desirable. The laser pulse rate is variable to fit the characteristics required during different surgical procedures. Furthermore, the present invention allows for selectively changing the energy density provided by each laser pulse by active attenuation.

The lasing device embodying the present invention includes a central processing unit, a laser resonator, a pulse modulator and pulse width feedback detectors. The central processing unit provides a switch activation command to the pulse modulator wherein the command corresponds to the desired pulse width. The modulator also receives a laser pulse produced by the laser resonator. The laser pulse has an initial pulse width and a wavelength which is compatible for transmission through an optical fiber. The modulator varies the width of the laser pulse so as to provide an output pulse having a pre-selected energy level. The pulse width feedback detectors monitor the width of the pulses received by the modulator as well as the output pulses so that the energy provided by the lasing device corresponds substantially to the pre-selected energy level.

BRIEF DESCRIPTION OF THE DRAWINGS

In the accompanying drawings that form part of the specification, and in which like numerals are employed to designate like parts throughout the same.

FIG. 4 is a block diagram illustrating a further embodiment of a variable pulse width lasing device in accordance with the present invention; and FIG. 5 is a schematic view which illustrates the laser energy paths within the variable pulse width lasing device of FIG. 4.

DESCRIPTION OF THE PREFERRED EMBODIMENTS

The present invention provides a lasing device and method which actively attenuate laser pulses and repeatably control the amount of laser energy which is transmitted through an optical fiber. The lasing device includes a central processing unit, a laser resonator, a pulse modulator and pulse width feedback detectors. The central processing unit provides a switch activation command to the modulator which also receives a laser pulse emitted from the laser resonator. The modulator varies the width of the laser pulse in response to the switch activation command, and thus provides an output pulse having a selected pulse width and at a selected energy level. The pulse width feedback detectors provide pulse width information verifying that the selected output energy provided by the lasing device is within established tolerances.

Figure 1:
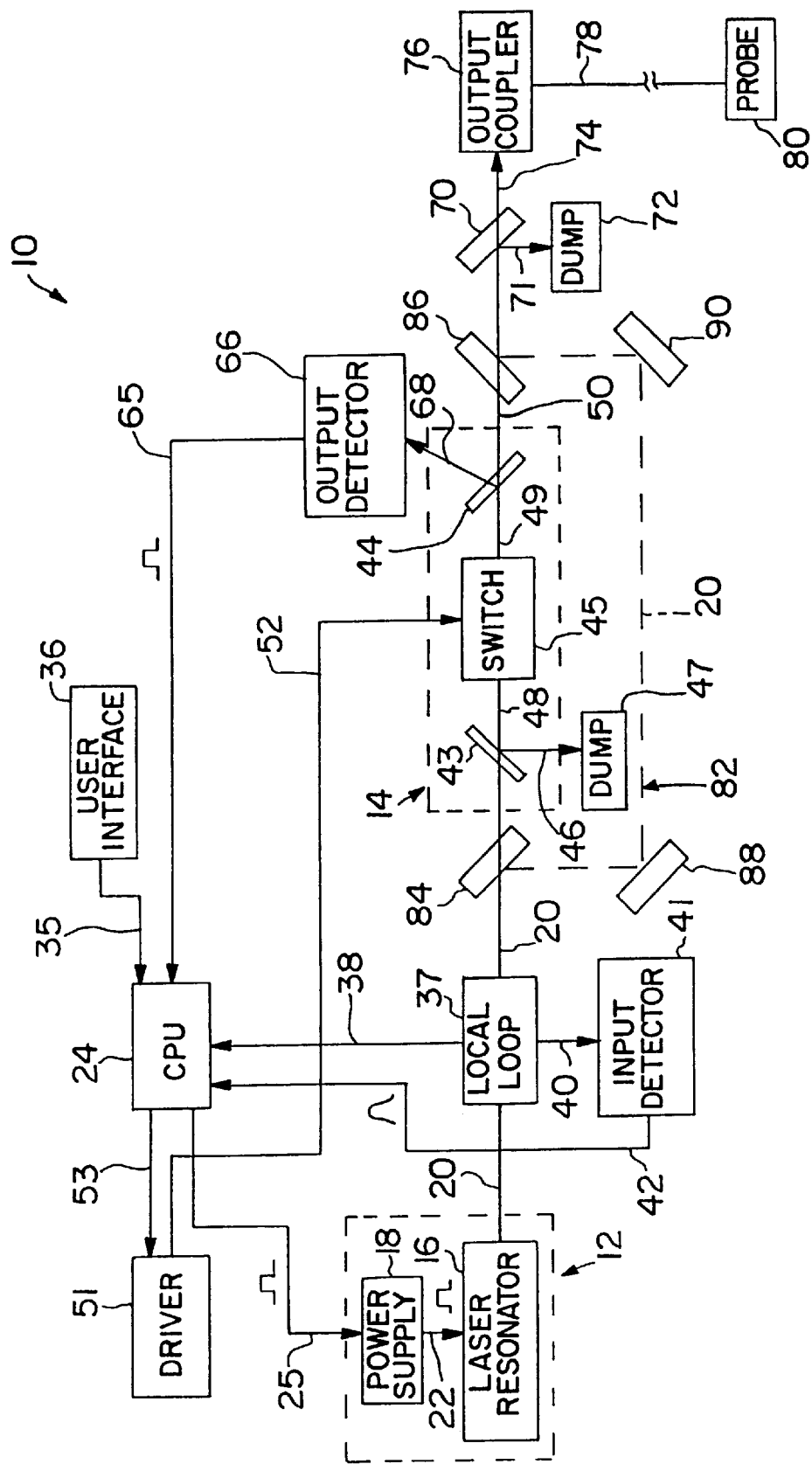
FIG. 1 is a block diagram illustrating a lasing device having a laser pulse generator for providing laser pulses, and a pulse width modulator for varying the width of the laser pulses.

Referring to the drawings, and particularly to FIG. 1, a variable pulse width lasing device 10 is depicted which includes a laser pulse generator 12 and a pulse width modulator 14. A single block within FIG. 1 may indicate several individual components and/or circuits which collectively perform a single function. Likewise, a single line may represent several individual signal or energy transmission paths for performing a particular operation.

The laser pulse generator 12 within FIG. 1 is of conventional construction and includes a laser resonator 16 and a power supply 18. The laser resonator 16 provides both the laser medium for generating laser light and the optical cavity for concentrating the light to stimulate the emission of pulsed laser energy 20.

The laser medium within the laser resonator 16 determines the wavelength of the laser energy 20. Wavelengths suitable for transmission through an optical fiber preferably are shorter than about 3 $\mu$m. Laser types which are suitable reside within both the excimer family of lasers and the near infra red, solid state family. Preferably, the medium is a solid state holmium laser such as yttrium scandium gallium garnet (Ho:YSGG) having an approximate wavelength of 2.088 $\mu$m or yttrium aluminum garnet (Ho:YAG) with an approximate wavelength of 2.127 $\mu$m.

The present invention should not, however, be limited to those applications wherein the laser medium necessarily provides a wavelength appropriate for transmission through an optical fiber. As such, suitable laser mediums may include those having a wavelength less than about 3.5 $\mu$m such as Helium-Neon at 3.39 $\mu$m.

The power supply 18 provides excitation energy 22 to the laser resonator 16 for exciting the laser medium. The excitation energy 22 is provided in the form required to excite the laser medium. For example, a gas medium typically requires that the power supply 18 provide an electrical discharge through the gas for causing excitation. Similarly, for a solid state medium such as holmium, the power supply 18 drives a device such as a flash lamp or diode laser for exciting the holmium laser medium.

The laser cavity within the laser resonator 16 is of conventional construction for use with the selected laser medium. For example, the resonator may provide both a total reflective mirror and a partially transparent mirror with the laser medium residing between the mirrors. The laser cavity may also include enhancements for focusing the wavelength emitted from the laser medium and stimulating the emission of pulsed laser energy 20 from the resonator 16.

The power supply 18 is commanded by a central processing unit 24, via trigger line 25, to provide excitation energy 22 for generating the pulsed laser energy 20. As indicated above, the excitation energy 22 is a pulse of electrical or light energy of sufficient intensity to excite the laser medium. The total excitation energy, excitation pulse length, and resulting peak power within each pulse of excitation energy 22 are proportional to the desired output energy. Each pulse of excitation energy 22 from the power supply 18 results in the generation of one pulse of laser energy 20 from the laser resonator 16.

Figure 2:
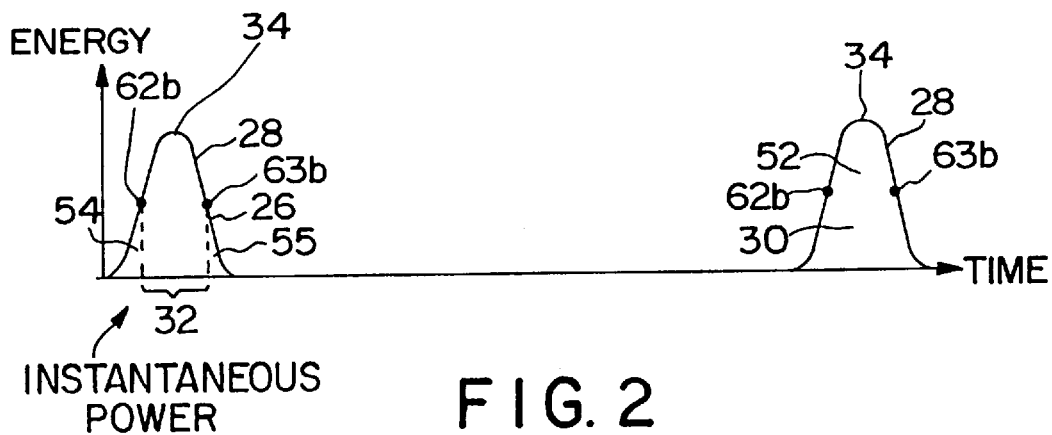
FIG. 2 depicts the energy output profile over time of laser pulses emitted from the laser resonator of FIG. 1.

FIG. 2 depicts two typical emitted pulses 26 of laser energy 20 from the laser resonator 16 wherein each emitted pulse is generated by an excitation pulse 22 from the power supply 18. The laser pulses 26 are generally equal to each other in energy output profile 28, total energy provided 30, measured full width at half-maximum pulse width 32, and peak power 34.

The energy output profile 28 of each pulse 26 generally has a semi-Gaussian shape wherein the output power increases, peaks, and then decreases. However, as appreciated by those skilled in the art, the profile of each pulse can have other various shapes depending on such factors as the laser medium used to generate the laser pulse, and the current and voltage pulse profiles used in generating the pulse.

In one embodiment, the resonator 16 of FIG. 1 is a conventional holmium:YAG resonator and is operated such that a range from about three (3) to eighty (80) laser energy pulses 26 can be provided per second with each pulse providing approximately 500 mJ of total energy 30. Preferably, the resonator 16 is operated at a pulse frequency such that fifty (50) pulses 26 are provided per second (i.e., 50 Hz).

In another preferred embodiment, the resonator 16 is a conventional erbium-yttrium aluminum garnet (Er-YAG) which has a wavelength of approximately 2.94 $\mu$m.

As indicated previously, the laser pulse frequency of the resonator 16 is controlled by the central processing unit 24. The processing unit 24 receives input and feedback signals from various elements within the lasing device as explained in detail further herein. The processing unit 24 uses the input and feedback signals to provide the desired laser pulse frequency and full width at half-maximum pulse width. As will be appreciated by those skilled in the art, the central processing unit 24 may consist of digital circuitry, analog circuity, or any combination thereof to analyze and control the various elements within the lasing device 10.

The processing unit 24 receives user input instructions 35 from a user interface 36 of conventional construction. The interface 36 may consist of input devices such as a computer terminal, a plurality of switches, a keyboard, a foot-switch, or any combination of such input devices. Preferably, the interface 36 allows for the selection of laser pulse frequency, full width at half-maximum pulse width, laser power output and length of dosage.

The pulsed laser energy 20 of the laser resonator 16 passes through a local loop 37 which detects the occurrence and magnitude of the peak power 34 of each laser pulse 26. The pulse information extracted by the local loop 37 is transmitted, via signal path 38, to the processing unit 24. Correspondingly, the pulse information is used by the central processing unit 24 to adjust the pulse rate of the laser resonator 16 so that it corresponds to the selected pulse frequency provided by the user interface 36. Furthermore, as explained in detail below, the peak power information from the local loop 37 is used by the processing unit 24 in spatially varying the width of each laser pulse 26 for providing the user selected laser power output.

Scattered light pulses 40 reflected by local loop 37 are received by an input detector 41. The intensity and duration of the scattered light pulses 40 correspond proportionately to the intensity and duration of the laser resonator energy pulses 20. Preferably, the input detector 41 consists of an ultra-fast photo-detector which converts the scattered light pulses 40 into corresponding electrical feedback signals 42 that contain pulse width information. The processing unit 24 receives the feedback signals 42 and uses the feedback in varying the width of each laser pulse in order to provide the user selected energy and power output as explained in detail further herein.

The laser energy 20 exiting the resonator 16 and passing through the local loop 37 is received by the modulator 14 wherein the initial or intrinsic pulse width 32 of each pulse 26 is adjusted such that the selected output pulse width is provided at a predetermined energy and power level. As illustrated in FIG. 1, the modulator 14 includes an input polarizer 43, output polarizer 44, and an electro-optic switch 45.

The pulsed laser energy 20 from the resonator 16 is first received by the input polarizer 43. A scatter portion 46 of the pulsed laser energy 20 is reflected by the polarizer 43 and received by a conventional beam dump 47.

That portion of the pulsed laser energy 20 which passes through the input polarizer 43 is horizontal or vertically polarized laser energy 48. The polarized energy 48 is received by the electro-optic switch 45, also referred to as a Pockels cell, which rotates the polarized pulsed laser energy when the switch is activated by being subjected to the stress of an electric field. The Pockels cell induces a phase shift on linearly polarized light between ordinary and extraordinary light rays that pass through the cell. This relative phase change is a linear function of the applied voltage. Thus, the amount of pulsed energy which passes through polarizer 44 is proportional to the degree of rotation provided by switch 45.

The electro-optic switch 45 rotates the polarized pulsed laser energy 48 by using an electric field to effect the refractive index of a nonlinear material within the switch such as a lithium niobate crystal. As known in the art, the inherent asymmetries within a crystal of this type result in it being birefringent. That is, linearly polarized light with a vertical electric field experiences a different refractive index than linearly polarized light with orthogonal polarization. The application of an electric field changes this birefringence, in effect rotating the polarized light as it passes through the crystal of the switch 45.

The linearly polarized laser energy 49 which passes through the crystal of the switch 45 is received by the second linear polarizing filter 44. When the switch 45 is activated, the degree of rotation is a fraction of the applied voltage. The voltage is chosen so that the Pockels cell behaves as a half-wave plate, rotating the polarization. This allows the polarized laser energy 49 to pass through the output polarizer 44, as output 50, at a modulated pulse width and a selected energy substantially without attenuation. Conversely, when the switch 45 is not activated, no polarization rotation occurs, thus the laser energy 49 does not pass through the output polarizer 44.

The modulator 14 spatially reduces the overall pulse characteristic of incoming pulses 28 which are shrunk to accommodate a user selected reduced energy level.

Although the pulse width modulator 14 of FIG. 1 is an electro-optical system which uses an electro-optical switch 45 and two beam polarizers 43 and 44, other types of pulse width modulators can be used. For example, an acousto-optic system which uses an acousto-optic switch for varying the width of each laser pulse, a mechanical Q-switch which uses a spinning mirror intercavity, or a dye cell Q-switch which uses a dye whose transmission depends on light intensity are also suitable. Each, however, is currently less effective and efficient than an electro-optical switch.

The electro-optical switch 45 within the modulator 14 is activated by driver 51 which, in turn, supplies a drive signal 52 to the switch 45 with adequate power for generating an electromagnetic field. The power provided by the drive signal 52 depends on the crystal used to rotate the polarization of the laser energy 48 and its size. Generally, however, the voltage of the drive signal 52 is in the range of three to eight kilowatts to fully rotate laser energy 48.

The driver 51 transmits power 52 to the modulator switch 45 when commanded by the processing unit 24. The switch activation command 53 from the processing unit 24 provides for varying the intrinsic pulse width 32 of the laser energy pulses 26 received by the pulse width modulator 14. Preferably, the time duration between the issuance of each switch activation command 53 corresponds to the desired pulse width of the output pulses from the modulator 14.

As stated previously, the processing unit 24 receives information as to a desired laser energy, power output and pulse width from the user interface 36. The processing unit 24 also receives from the local loop 37 information on the amount of peak energy 34 generated by the laser resonator 16 for each laser pulse 26.

The peak energy 34 of each laser pulse 26 corresponds directly to the pulse width 32 since the total energy 30 and output profile 28 of each pulse is constant. Further, the front tail 54 and the rear tail 55 of each input pulse 26 defines the natural pulse width characteristic.

Figure 3:
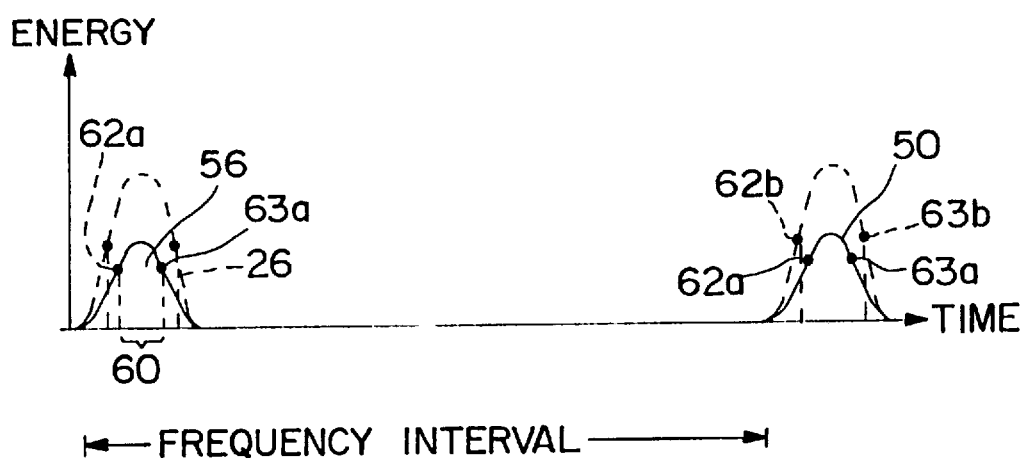
FIG. 3 depicts the energy output profile over time of the laser pulses of FIG. 2 after passing though the pulse width modulator of FIG. 1.

As shown in FIG. 3, only the spatially modulated portion 56 of each laser pulse 26 passes through the modulator 14 as an output pulse 50. Each spatially modulated output energy pulse 50 is the result of timing the input energy pulse 26 with the switch 45 to maximize the resulting output and provide the desired pulse width. The correlation between the natural energy pulse 26 and the modulated energy pulse 50 is a point to point spatial, proportional reduction of the natural energy pulse. The resulting pulse width 60 is determined by full width at half maximum (FWHM) points 62a and 63a which correspond to the initial width between points 62b and 63b, respectively, of each initial pulse 26. As such, the processing unit 24 can decrease or increase the energy provided by the laser output pulses by varying the electric field of the modulator 14. Further, a train of these modulated pulses 50 over time and at a specified frequency corresponds to the seconds of lasing (i.e., dosage).

The feedback provided by the local loop 37 regarding peak energy 34 is used by the central processing unit 24 to determine the amount of spatial reduction required for achieving the desired laser power output and energy per pulse. The pulse width 32 of each pulse 26 can vary according to the user's selection. Therefore, an increase or a decrease in the peak energy 34 will result in a corresponding decrease or increase, respectively, in the pulse width 32.

Stated another way, the peak energy is attenuated by pulse width modulator 14 and is modulated as well. This allows the selection of a reduced pulse width 60 and a relatively lower energy level. As an example, the user may select a pulse width of 60 microseconds and then select a range of output energies from 1 mJ to 250 mJ. Likewise, the user may fix the energy and vary the pulse width.

The above information about the holmium YAG laser, along with the measured peak pulse energy 34 information from the local loop 37 and the initial pulse width information from the input pulse width detector 41 is used by the central processing unit 24 to determine the required parameters for proper spatial reduction to satisfy the laser energy, pulse width and power output requirement as requested by the user interface 36.

As indicated above and as shown in FIGS. 2 and 3, the portion of the front tail 54 and the rear tail 55 of each pulse 26 establishes the natural pulse and energy characteristics that are spatially reduced to provide the desired laser power output and energy per pulse. Determining the full width at half maximum 32 provides an approximate description of the Gaussian shape of the laser pulse profile 28 of each pulse 26. The full width at half maximum is the energy provided as each laser pulse profile 28 is equal to, or greater than, half the maximum power 34 provided by the laser pulse. As shown in FIG. 2, this is the energy provided between points 62b and 63b of each laser pulse profile 28.

Each pulse 26 received by the modulator 14 is spatially varied to provide a modulated portion 50 having an amount of energy 56 which corresponds to the selected laser power output, energy per pulse and pulse width provided by the user interface 36. Preferably, the amount of energy 56 provided by using a holmium:YAG laser is in the range of from about 0.1 mJ to 1500 mJ. However, higher energy levels and ranges may be desired such as from about 0.1 mJ to about 3500 mJ.

Selection of the amount of energy 56 for a given frequency within each output pulse 50 may be provided by a user interface consisting of a foot-switch wherein the amount of energy provided is responsive to the foot-pressure applied to the foot-switch such that the energy is increased proportionately to an increase in foot-pressure. In operation, the foot-switch 36 generates a signal received by the central processing unit 24 which corresponds to the desired energy level 56 of the output pulses 50. Alternatively, the user interface 36 may provide for selecting finite pulse widths such as 50 $\mu$sec, 250 $\mu$sec, 150 $\mu$sec and 250 $\mu$sec.

Feedback 65 to the central processing unit 24 for monitoring the modulation of the laser pulses 26 is provided by an output detector 66 which may consist of an ultra-fast photo-detector. The output detector 66 is positioned such that it receives the scattered light 68 from the output polarizer 44 of the modulator 14. Preferably, the output detection signal 65 transmitted by detector 66 corresponds to the modulated pulse width 60 of the output laser pulses 50 being emitted from the modulator 14.

The feedback 65 provided by the output detector 66 is used by the central processing unit 24 to compare the laser output energy provided by the pulses 50 with the desired energy output and pulse width. Based on this information, the central processing unit 24 makes adjustments such that the energy and pulse width provided by the output pulses 50 is of the desired value.

The laser output pulses 50 from the modulator 14 can be received by an attenuator 70 which provides for further reduction of the energy of the pulses. The power is reduced in order to achieve a stable relatively low energy output level of 0.01 mJ to 100 mJ. Conventional resonator designs must be operated at higher output levels. The excess laser energy 71 removed by the attenuator 70 is transmitted to the convention laser beam dump 72 for absorbing the unwanted energy. The attenuator 70 is controlled by the central processing unit 24 via a solenoid, or like device, to move the attenuator in or out of the laser beam path based upon the input of a selected output power level.

The laser pulses 74 passing from the attenuator 68 are received by a conventional output coupler 76 which allows the laser energy beam to be focused into an energy transfer medium such as a conventional optical fiber 78. The energy transferred by the fiber 78 may be directed, and emitted from the distal end of optical fiber 80 or, alternatively a hollow needle containing an optical fiber, a transdermal probe, a scanning device, or the like, can be used.

Furthermore, the optical device 10 is provided with a full energy bypass route 82 around the pulse width modulator 14 for allowing the laser radiation 20 which passes through the local loop 37 to proceed directly to the attenuator 70. The bypass route 82 is activated by a command from the user interface 36 to the central processing unit 24. Once activated by a bypass command from the central processing unit 24, pop-up shutters 84 and 86 are extended into the laser beam path 20. The laser energy passing through the local loop 37 is reflected by pop-up shutter 84 towards a fixed mirror 88. The laser energy reflected by the fixed mirror 88 is received by another fixed mirror 90 and directed towards pop-up shutter 86 wherein the energy is finally directed to the attenuator 70. Thus, the full laser energy passing through the local loop 37 is directed around the modulator 14.

The above described variable pulse width lasing device provides for modulation of the pulse width in order to reduce the collateral thermal damage, control the depth of penetration, and achieve "equivalent tissue effect" to that of $CO_2$ and erbium. Since the water absorption characteristics of $CO_2$, erbium and excimer are different and substantially less than holmium, a substantial reduction in energy per pulse and a reduction in pulse width from its intrinsic form is required to obtain "equivalent" tissue effect. In effect, limiting the fringe (outer edge) energy, by squaring off the pulse, and using an electro-optical Q-switched device for energy reduction and stability, can provide a controlled tissue effect of either CO$_2$ or erbium or excimer or holmium. The goal is to reduce the energy scattering and transmission at and within the tissue site and produce a clean crater, equivalent to those obtained with CO$_2$, erbium and excimer.

Turning to FIGS. 4 and 5, another embodiment of a lasing device 110 is provided in accordance with the present invention. The lasing device 110 is similar to the device 10 depicted in FIG. 1 except for the addition of two resonators 16*a*,16*b*, a co-axial positioning device 91, and a conventional beam splitter 92. Correspondingly, the same numerals used in FIG. 1 are also used in FIGS. 4 and 5 to depict structural elements which are similar in function to those described hereinabove.

The two laser resonators 16*a* and 16*b* are similar to one other. As explained above, each resonator 16*a*,16*b* has an optical cavity 19 residing between a total reflective mirror 21 and a partially transparent mirror 23.

The two laser resonators 16*a* and 16*b* each alternately produce pulsed laser energy 20*a* and 20*b*, respectively, which is received by the co-axial positioning device 91 for constructing a composite "beam" of pulsed laser energy beam 20 which is directed along a single axis.

As described in commonly owned U.S. Pat. No. 4,387,211 to Saadatmanesh et al., and incorporated herein by reference, the co-axial positioning device 91 may include a conventional laser energy reflecting mirror 93 and a single rotary reflector 94 with plural blades. The mirror 93 reflects laser energy path 20*b* towards laser energy path 20*a* such that the laser energy paths 20*a* and 20*b* intersect at a right angle generally at an intersection region 95. Although the laser energy paths 20*a* and 20*b* are aligned to intersect in the region 95, the two resonators 16*a* and 16*b* are operated at different times, as described hereinafter, so that the energy pulses from each resonator do not coincide in time but only in space.

The reflector 94 is provided at the path interception region 95 for intercepting energy path 20*b* and directing the pulsed laser energy along the axis defined by energy path 20*a*. The reflector 94 is rotated by a drive motor 96. Preferably, the motor 96 is an adjustable speed electric motor which is controlled by the central processing unit 24 and is capable of rotating through a range of rotational speeds.

The rotational position of the rotary reflector 94 is transmitted by the co-axial positioned device 91 to the central processing unit 24. The firing of the laser resonators 16*a*,16*b* is controlled by the central processing unit 24, via power supply 18, such that laser energy 20*b* is emitted by resonator 16*b* only as a blade of the reflector 94 rotates through the path interception region 95. The central processing unit 24 also operates laser resonator 16*a* such that laser energy 20*a* is emitted only when the reflecting member 94 has rotated beyond the path interception region 95 and thus the laser energy 20*a* passes unobstructed between the blades of the reflector. Therefore, the embodiment depicted in FIGS. 4 and 5 can deliver laser energy 20 at a relatively faster pulse repetition rate than the embodiment depicted in FIG. 1 because two resonators in device 110 can be operated to alternately provide the pulses 26 of laser energy 20.

The laser energy 20 is received by the local loop 37 which is depicted in FIG. 5 to include a wedge 97, a mirror 98, and a detector 99. The laser energy 20 which passes through the local loop 37 is directed through the wedge 97 such that a portion of the laser energy is reflected by the wedge and bounced by mirror 98 onto detector 99. The detector 99 registers the occurrence and magnitude of the peak power 34 of each laser pulse 26. The pulse information extracted by detector 99 is transmitted, via signal path 38, to the processing unit 24. The detector 99 is of conventional design and thus the detailed design, construction, and operation of such a detector forms no part of the present invention.

The output detector 66 is positioned to receive the scattered light 68 from the output polarizer 44 for detecting pulse width and therefore, attenuated laser energy pulses 26. Preferably, the pulse width detection signal 65 transmitted by the output detector 66 to the central processing unit 24 indicates the resulting pulse width of energy output pulses 50.

The output pulses 50 from the modulator 14 are received by the attenuator 70 and the splitter 92. As stated above, the attenuator 70 further reduces the energy of the output pulses 50. The attenuator 70 and the splitter 92 are of conventional construction and, as known in the art, may include components such as lenses, windows, prisms, mirrors, coatings, and the like. Thus, the detailed design, construction, and operation of such components per se forms no part of the present invention.

It will be readily apparent from the foregoing detailed description of the invention and from the illustrations thereof that numerous variations and modifications may be effected without departing from the true spirit and scope of the novel concepts or principles of this invention.

We claim:

1. A variable pulse width lasing device comprising:
    a central processing unit responsive to a detection signal for transmitting a switch activation command;
    a laser resonator for producing a laser pulse having an initial pulse width and a wavelength which is compatible for transmission through an optical fiber;
    a pulse width modulator which receives said laser pulse and is responsive to said switch activation command for varying said initial laser pulse width after said laser pulse is produced by said resonator to provide an output pulse having predetermined energy and pulse width; and
    a detector responsive to said output pulse for producing said detection signal.

2. The variable pulse width lasing device of claim 1, wherein said laser resonator is an erbium: YAG resonator.

3. The variable pulse width lasing device of claim 1, wherein said laser resonator is an erbium: YSGG resonator.

4. The variable pulse width lasing device of claim 1, wherein said laser resonator is a holmium:YAG resonator.

5. The variable pulse width lasing device of claim 1, wherein said laser resonator is a holmium:YSGG resonator.

6. The variable pulse width lasing device of claim 1, wherein said laser resonator is an excimer resonator.

7. The variable pulse width lasing device of claim 1, wherein said wavelength is less than 3.5 μm.

8. The variable pulse width lasing device of claim 1, wherein said modulator includes an electrooptic switch.

9. The variable pulse width lasing device of claim 1, wherein said modulator incudes an acousto-optic switch.

10. The variable pulse width lasing device of claim 1, wherein said modulator incudes a dye cell Q-switch.

11. The variable pulse width lasing device of claim 1, further comprising a bypass route, responsive to a bypass command from said central processing unit, for directing said laser pulse around said modulator.

12. The variable pulse width lasing device of claim 1, further comprising a user interface for transmitting user input instructions to said processing unit.

13. The variable pulse width lasing device of claim 1, further including another laser resonator for producing a second laser pulse, said second laser pulse received by said modulator for providing a second output pulse having said selected amount of energy level and pulse width.

14. The variable pulse width lasing device of claim 1, wherein said detector is responsive to the pulse width of said output pulse.

15. The variable pulse width lasing device of claim 1, wherein said laser resonator provides a plurality of laser pulses at a selected frequency.

16. The variable pulse width lasing device of claim 15, wherein said selected frequency is in the range of about 3 Hz to 80 Hz.

17. The variable pulse width lasing device of claim 1, wherein said selected amount of energy is in the range of about 0.1 mJ to about 3500 mJ.

18. The variable pulse width lasing device of claim 10, wherein said modulator further includes two beam polarizers.

19. The variable pulse width lasing device of claim 1, wherein said modulator includes a mechanical Q-switch.

20. The variable pulse width lasing device of claim 19, wherein said user input instructions include laser pulse frequency, laser pulse width, laser energy output and laser power output.

21. The variable pulse width lasing device of claim 19, wherein said user interface includes a foot-switch whose degree of foot-pressure generates a signal to the central processing unit which corresponds to the energy level and pulse width of said output pulse.

22. A lasing device comprising:
   a user interface for transmitting user input instructions;
   a central processing unit responsive to said user input instructions and a detection signal for transmitting a switch activation command;
   a laser resonator for producing a laser pulse at a wavelength less than 3.5 µm;
   a pulse modulator which receives said laser pulse and is responsive to said switch activation command for providing an output pulse having a selected pulse width and amount of energy after said laser pulse is produced by said resonator; and
   a detector responsive to said output pulse for producing said detection signal.

23. The lasing device of claim 22, wherein said laser resonator provides a plurality of laser pulses at a selected frequency in the range of about 3 Hz to 80 Hz.

24. The lasing device of claim 22, wherein said laser resonator is an erbium: YAG resonator.

25. The lasing device of claim 22, wherein said laser resonator is an erbium: YSGG resonator.

26. The lasing device of claim 22, wherein said laser resonator is an excimer resonator.

27. The lasing device of claim 22, wherein said selected amount of energy is in the range of from 0.1 mJ to 3500 mJ.

28. The lasing device of claim 22, wherein said modulator includes an electro-optic switch.

29. The lasing device of claim 22, wherein said modulator incudes a mechanical Q-switch.

30. The lasing device of claim 22, wherein said modulator incudes a dye cell Q-switch.

31. The lasing device of claim 22, further comprising a bypass route, responsive to a bypass command from said central processing unit, for directing said laser pulse around said modulator.

32. The lasing device of claim 22, wherein said user input instructions include laser pulse frequency, pulse width, laser energy and laser power output.

33. The lasing device of claim 22, wherein said user interface includes a foot-switch.

34. The lasing device of claim 22, further comprising another laser resonator for producing a second laser pulse, said second laser pulse received by said modulator to provide a second output pulse having a selected pulse width and amount of energy.

35. The lasing device of claim 22, wherein said detector monitors a selected amount of energy within said output pulse.

36. A method which comprises the steps of:
   producing a laser pulse having an initial pulse width;
   transmitting a detection signal in response to said initial pulse width;
   transmitting a switch activation command responsive to said detection signal;
   varying said initial pulse width in response to said switch activation command to provide an output pulse having a predetermined energy and pulse width;
   transmitting an output detection signal in response to said output pulse.

37. The method of claim 36, further including the step of transmitting a user input instruction to control said switch activation command.

38. The method of claim 36, further including the steps of generating a second laser pulse and directing said second laser pulse around a switch.

39. The method of claim 36, wherein varying said initial pulse width includes the step of passing said laser pulse through an input polarizer to provide polarized laser energy.

40. The method of claim 39, wherein varying said initial pulse width further includes the step of rotating said polarized laser energy.

41. The method of claim 40, wherein varying said initial pulse width further includes the step of passing said polarized laser energy through an output polarizer.

* * * * *